United States Patent [19]

Sparrow et al.

[11] Patent Number: 5,084,509
[45] Date of Patent: Jan. 28, 1992

[54] POLYAMIDE BOUND PROTIDE, METHOD OF USE THEREOF AND KIT

[75] Inventors: James T. Sparrow, Houston; Patrick Kanda; Ronald C. Kennedy, both of San Antonio, all of Tex.

[73] Assignee: Baylor College of Medicine, Houston, Tex.

[21] Appl. No.: 614,857

[22] Filed: Nov. 16, 1990

Related U.S. Application Data

[60] Division of Ser. No. 368,708, Jun. 19, 1989, Pat. No. 4,973,638, which is a continuation-in-part of Ser. No. 858,216, Apr. 30, 1986, abandoned.

[51] Int. Cl.$^5$ ............................................. C08G 63/48
[52] U.S. Cl. ..................................... 525/54.1; 525/54.11
[58] Field of Search ............................... 525/54.1, 54.11

[56] References Cited

U.S. PATENT DOCUMENTS

| | | |
|---|---|---|
| 2,123,013 | 6/1983 | Handa et al. |
| 2,134,531 | 1/1984 | Furnuno et al. |
| 2,576,502 | 11/1951 | Dalton |
| 2,893,970 | 7/1959 | Caldwell et al. |
| 3,061,595 | 10/1962 | Dorion et al. |
| 3,912,607 | 10/1975 | Communal et al. |
| 3,925,267 | 12/1975 | Coupek et al. |
| 4,074,039 | 2/1978 | Lim et al. |
| 4,138,539 | 2/1979 | Landolt et al. |
| 4,172,066 | 10/1979 | Zweigle et al. |
| 4,528,348 | 7/1985 | Turner et al. |
| 4,658,000 | 4/1987 | Tyihak et al. |

OTHER PUBLICATIONS

Prince, A. M., et al., 79 Proc. Natl. Acad. Sci. U.S.A. 579 (1982).
Sanchez, Y., et al., 18 Intervirology 209 (1982).
Arshady, R., et al., 1979 J.C.S. Chem. Comm. 425 (1979).
Dreesman, G. R., et al., 295 Nature 158 (1982).
Lerner, R. A., et al., 78 Proc. Natl. Acad. Sci. U.S.A. 3403 (1981).
Merrifield, R. B., "Solid-phase Peptide Synthesis," 32 Adv. Enzymology 221 (1969).
Atherton, E., et al., 97 J. Amer. Chem. Soc. 6584 (1975).
Stahl, G. L., et al., 101 J. Am. Chem. Soc. 5383 (1979).

*Primary Examiner*—Joseph L. Schofer
*Assistant Examiner*—N. Sarofim
*Attorney, Agent, or Firm*—Cox & Smith, Incorporated

[57] ABSTRACT

A polyamide resin for use in peptide and protein synthesis, and a method of preparing and using same. The polyamide resin is prepared by mixing a dimethylacrylamide monomer with an N-acrylyl-diaminoalkane functional monomer in an aqueous solution together with a cross-linker and emulsifying the aqueous solution in an organic solvent. An initiator and a promoter are added to polymerize the N-acrylyl-diaminoalkane functional monomer, dimethylacrylamide monomer, and cross-linker in the form of beads. The pH of the mixture is controlled during the polymerization. The beads are used as a solid phase for peptide and protein synthesis according to methods known in the art. The conjugate of the polyamide resin and the synthesized peptide or protein is used directly for immunoassays or immunization without the need for separation of the peptide or protein from the resin and subsequent purification.

22 Claims, 1 Drawing Sheet

POLYAMIDE BOUND PROTIDE, METHOD OF USE THEREOF AND KIT

STATEMENT REGARDING GOVERNMENT SUPPORT

This invention was made with Government support under one or more of the following NIH grants: 2 RO, HL 30064-03; HL 27341-03; HL 17269. The Government has certain rights in this invention.

CROSS REFERENCE TO RELATED APPLICATION

This is a divisional application of copending application Ser. No. 07/368,708 filed on June 19, 1989, now U.S. Pat. No. 4,973,638, which is a continuation-in-part of application Ser. No. 858,216, filed on Apr. 30, 1986 now abandoned, entitled POLYAMIDE RESIN AND METHOD FOR PREPARATION OF REAGENTS FOR IMMUNODIAGNOSTIC USE.

BACKGROUND OF THE INVENTION

The present invention relates to the synthesis and use of synthetic peptides and proteins to induce an immune response in experimental animals. More particularly, the present invention relates to an improved polyamide resin, a method of making that improved polyamide resin, a method of inducing an immune response in an experimental animal using a conjugate of a peptide or protein synthesized on that improved resin, and the use of the peptide-improved resin conjugate for immunodiagnostic purposes.

Solid phase peptide synthesis is a valuable tool for investigating the structure and mechanism of action of proteins. Most such synthetic methods involve the use of a cross-linked polystyrene based resin as the solid phase to which the peptide is anchored during assembly, usually through a linker molecule. Assembly is accomplished by a repetitive cycle of adding a protected amino acid to the solid phase, selectively removing (deprotecting) a protective group on that amino acid, and adding additional suitably protected amino acids (for a review, see Merrifield, R. B., "Solid-phase Peptide Synthesis", 32 Adv. Enzymology 221 (1969)).

Although cross-linked, polystyrene based resins are commonly used as supports in solid phase peptide synthesis, their relatively hydrophobic character in comparison to the polar organic media required to solubilize reactants can be problematic in peptide chain assembly. Such media may freely solvate the growing peptide, yet incompletely swell the polystyrene matrix. Within the polymer lattice, impaired diffusion of reagents and steric hindrance can contribute to lowered efficiency during coupling cycles, which, on a repeated basis, lowers final yields appreciably. During the early stages of assembly, when the resin to peptide mass ratio is high and the physical properties of the support dominate, this lowered efficiency is particularly acute.

Those shortcomings led to the development of a cross-linked, polydimethylacrylamide based support which is highly polar in character and is freely permeated by the requisite solvents for peptide synthesis. Atherton, E., et al., 97 J. Amer. Chem. Soc. 6584 (1975); Arshady, R., et al., 1979 J.C.S. Chem. Comm. 425 (1979). That polyamide resin, as the amino methyl derivative, can accommodate synthetic schemes incorporating alternate protection strategies through selection of the appropriate linker molecule, which links the C-terminal residue to the support. The peptide or protein thus synthesized, which will be referred to throughout the present disclosure as a "protide", can be used in a number of investigative applications.

Of particular interest to the present invention is the use of the protide as an immunogen. It has previously been demonstrated that synthetic peptides analogous to sequences contained in viral encoded proteins have proven useful for identification of native antigen determinants associated with such proteins. Several laboratories have reported studies on the antigenic activity of various HBsAg synthetic peptides. (Dreesman, G. R., et al., 295 Nature 158 (1982); Lerner, R. A., et al. 78 Proc. Natl. Acad. Sci. USA 3403 (1981); Prince, A. M., et al., 79 Proc. Natl. Acad. Sci. USA 579 (1982).) The induction of an antibody response to HBsAg, using such peptides, proved to be relatively weak, but could be enhanced through coupling of peptides to a carrier protein prior to immunization. Lerner, et al., supra; Sanchez, Y., et al., 18 Intervirology 209 (1982). Because the prediction of potential antigenic determinants of immunogenic proteins based on primary sequences analysis is not exact, the identification of putative epitopes through trial and error can be laborious. A method which involves the delineation of native antigenic sequences with synthetic peptides which does not require purification of the synthetic peptide and coupling of the peptide to carrier proteins offers significant advantages. It is, therefore, an object of the present invention to provide an improved polyamide resin for solid phase protide synthesis which is particularly useful in the mapping of the antigenic determinants of a protein as a result of the elimination of the steps of separation of the protide from the resin and the subsequent purification of the protide before the use of the protide in a binding assay.

It is another object of the present invention to provide an improved polyamide resin, and method for the preparation thereof, upon which a protide can be synthesized using solid phase synthetic methods which can be injected into an experimental animal to induce an immunogenic response without separation of the protide from the resin.

It is another object of the present invention to provide a polyamide resin-protide conjugate for use in in vitro immunological assays.

Another object of the present invention is to provide a method of inducing an immunogenic response in an experimental animal with a synthetic peptide or protein comprising preparing a polyamide resin, synthesizing a peptide or protein on that polyamide resin-synthetic peptide or synthetic protein conjugate.

These and other objects and advantages of the present invention will be clear to those skilled in the art from the following description.

SUMMARY OF THE INVENTION

These objects are accomplished by providing a method of preparing a polyamide resin for solid phase protide synthesis comprising polymerizing a dimethylacrylamide monomer, an aminoalkene or N-acrylyldiaminoalkane monomer, and a cross-linker. The monomeric components are first mixed in an aqueous solution whose pH is adjusted to about 6.0. An initiator is added to the aqueous solution. The mixture is then emulsified in an organic solution to form micelles in which the polymerization reaction takes place. An aqueous solution of the promoter whose pH is adjusted to about 6.0 is added to accelerate the polymerization. The beads of polyamide resin thus formed are then isolated by washing both organic and aqueous solvents away and used as the solid phase for synthesis of a protide.

Also provided is a method of inducing an immunogenic response in an experimental animal comprising preparing a polyamide resin, synthesizing a protide on the polyamide resin, and immunizing an experimental animal with the polyamide resin-protide conjugate.

An in vitro diagnostic assay is also provided which comprises preparing a polyamide resin, synthesizing a protide on the resin to form a polyamide resin-protide conjugate, and contacting the polyamide resin-protide conjugate with a body fluid suspected of containing antibodies capable of binding specifically to the protide. The bound antibodies are then detected by using, for instance, an enzyme linked immunosorbent assay.

phase synthetic methods. Hydrazine has also been used to separate the protide from the resin (Kessler, W. and B. Iselin, 49 Helv. Chim. Acta 1330 (1966)) as have various ammonolytic (Manning, M., 90 J. Am. Chem. Soc. 1348 (1968)) and other methods. However, those methods all require that appropriate steps be taken to avoid damage to the protide resulting from cleavage followed by purification of the protide from the by-products of the synthesis, including amino acids, short peptides, decomposition products of the resin, and sometimes, peptides containing incompletely removed protecting groups. Although purification can sometimes be accomplished by a direct crystallization, in syntheses in which the contaminating peptides are of approximately the same size and composition as the desired product, more selective techniques must be employed. Regardless of the method of separation and purification, those requirements add time-consuming steps to the synthesis which often lower the total yield of protide. The method of the present invention requires no such separation and purification, thereby decreasing the amount of time required to accomplish the synthesis and raising the protide yield.

The polyamide resin of the present invention is prepared by cross-linking a commercially available dimethylacrylamide monomer in aqueous solution using a diaminoalkane, preferably a diaminoalkane having alkenoyl groups at either end of the molecule such as N,N'-bisalkenoyl-diaminoalkane, as a cross-linker. In a presently preferred embodiment, the cross-linker is either N,N'-bisacrylyl-1,3-diaminopropane or N,N'-bisacrylyl-1,4-diaminobutane prepared according to the method of Halpern and Sparrow (J. A. Halpern and J. T. Sparrow, 10 Synthetic Comm. 569 (1980)), hereby incorporated in its totality by this specific reference thereto:

DETAILED DESCRIPTION OF THE INVENTION

As noted above, the term "protide", as used herein, refers to both the peptides and proteins which are synthesized according to the method of the present invention. A significant advantage of the method of the present invention is that the protide-polyamide resin conjugate can be used to induce an immunogenic response in a mammal without being separated from the resin and purified.

The usual method of coupling a protide to a polystyrene based resin for solid phase synthesis is through a benzyl ester derivative, and separation of the completed protide from the resin is usually accomplished by either acidic or basic cleavage. Benzyl esters are susceptible to several such methods of cleavage, but are also stable throughout the multiple deprotection, neutralization and coupling reactions which are characteristic of solid The use of the propane analog (n=3) is preferred because that analog yields a polymer of larger pore size and improved swelling properties during protide synthesis than the polymer obtained by use of the ethyl analog. However, it will be understood by those skilled in the art who have the benefit of this disclosure that the other diaminoalkanes listed in that report, N,N'-bisacrylyl-1,2-diaminoethane and N,N'-bisacrylyl-1,6-diaminohexane, as well as other diaminoalkanes, are also appropriate for use in the preparation of the resin of the present invention.

A functional monomer is also included in the cross-linked resin of the present invention. The term "functional monomer" refers to those amino alkenes and N-acrylyl diaminoalkanes, which are used to anchor the C-terminal amino acid of a synthetic protide to the resin. The functional monomer can be protected with the methylsulfonylethyloxycarbonyl (MSC) group (see Tesser, G. I. and I. C. Balvert-Geers, 7 Int. J. Peptide Protein Res. 295 (1975), in order to prevent reaction of the free amino group during the polymerization process. Those functional monomers are prepared by reaction of the commercially available chloride derivative of the MSC with the aminoalkene or N-acrylyl-diamino alkane to form the urethane. The urethane, in the case of allylamine, is readily purified by passage through silicic acid in chloroform and crystallizes in plates from methylene chloride:hexane, and the MSC protective group is subsequently removed with base:

The MSC-protected functional monomer is found to be completely soluble in the aqueous solution containing the other polymerization monomers. However, the MSC group is not required if the pH is sufficiently acidic to maintain the amino group of the functional monomer in a protonated state (i.e. a pH between 6.0 and 7.5).

The amount of functional monomer added is selected to yield a resin substitution of between about 0.1 mmol and about 0.7 mmol per gram of resin, and preferably in the range of about 0.2 mmol to about 0.7 mmol per gram of resin. For instance, loadings of about 0.2-0.4 mEq/g resin were realized when the level of MSC-allylamine was increased to 20 mole percent. The initiator can be any of the initiators known to those skilled in the art such as a persulfate or riboflavin, and is preferably ammonium persulfate.

In a presently preferred embodiment of the present invention, the functional monomer is an N-acrylyl-diaminoalkane.

Because the above-described substances are combined in aqueous solution, they are collectively referred to as "the aqueous phase". The next step in the preparation of the polyamide resin of the present invention is to combine the aqueous phase with an organic phase. The term "organic phase" refers to an organic solvent which, when combined with the aqueous phase and stirred, results in a suspension from which the resin of the present invention is obtained. In a presently preferred embodiment, the organic phase comprises a mixture of hexane and carbon tetrachloride.

An emulsifier is added during the stirring to allow for the formation of beads of uniform size. The emulsifier can be any detergent known to those skilled in the art, and in a presently preferred embodiment, is either sorbitan sesquioleate, sorbitan monolaurate or sorbitan monodecanoate. The amount of detergent added is adjusted to give a spherical resin of approximately uniform size. A decrease in the amount of detergent results in an emulsion which yields increased amounts of larger, amorphous material, which could contribute to a reduction to the internal growing chains of amino acids. An increase in the amount of detergent increases the amount of fine material, which is difficult to remove without the loss of significant amounts of the resin. Those fines clog the reaction vessels of the peptide synthesizer as well as the associated lines and valves.

A solution of promoter titrated to pH between 6.0 and 7.5 is added to promote the polymerization of the monomers in the suspension, resulting in the formation of beads of the polyamide resin. A number of promoters are known to those skilled in the art, but particular success in preparing the polyamide resin of the present invention has been obtained with N,N,N',N'-tetramethylethylenediamine (TEMED). In a presently preferred method of preparing the resin, the pH of the promoter solution is adjusted prior to polymerization with dilute mineral acid to about 6.0, but acceptable resins have been prepared at a pH from about 6.0 up to about 7.5. The resulting beads are then filtered and washed, the MSC group (if present) is removed with base, and the beads are dried. The beads may then be sifted through a mesh sieve to insure relatively uniform size. Overall yields using the method of the present invention ranged from about 87% to 94% from starting monomers.

The aminomethyl, cross-linked polydimethylacrylamide resin of the present invention, therefore, takes the following general structure, depending upon the identity of the functional monomer:

Where A is either $-(CH_2)-_xNH_2 \cdot HCl$ in the case of an aminoalkane, where x is an integer, the presently preferred integer being 1, (i.e., when allylamine is used as the functional monomer) or $-CONH-(CH_2)-_yNH_2 \cdot HCl$ in the case of an N-acrylyl-aminoalkane functional monomer, where y is an integer, the presently preferred integer being 6, (i.e., when N-acrylyl-1,6-diaminohexane is used as the functional monomer) and n is an integer, the presently preferred integer being either 3 or 4 (i.e., when either N, N'-bisacrylyl-1, 3- diaminopropane or N,N'-bisacrylyl-1, 4-diaminobutane is used as the cross-linker).

This structure provides maximum exposure of the protide in an aqueous solution, and the resin-polymer backbone does not restrict the protide conformationally. The exposure of the protide is the result of the ability of the polyamide resin to swell to many times its dry bed volume when highly solvated by water.

Protides are then synthesized on the beads by coupling either directly to the resin, or to a linker which is attached to the resin, with an activator. The term "linker" refers to a linking group which links the carboxyl group of the first amino acid of the protide to the polymeric resin. In the presently preferred embodiment, this linker is an oxyalkyl benzoic acid (OBA) to which one or more amino acid residues are coupled to serve as the first amino acids in the protide chain. Because the OBA linker is used to attach the C-terminal amino acid of the first amino acid to the polyamide resin of the present invention, anhydrous hydrogen fluoride can be used to remove the side chain protecting groups from the protide without significant loss of the protide from the resin. In the below-described examples, the first amino acid of choice is glycine, which is protected with the t-butyloxycarbonyl (t-Boc) protecting group, but it will be understood by those skilled in the art who have the benefit of this disclosure that the amino acid could be any amino acid, such as, the amino acid which is the first amino acid in the protide to be synthesized, and that other protecting groups are equally suitable. A short chain of amino acids could also be used which function as a spacer between the protide and the resin-polymer backbone. Polyglycine is one such chain of amino acids which can be so used as is polyalanine. For synthesis of more complicated protides, i.e., those which are comprised of multiple chains, or when it is desired to synthesize multiple epitopes as may be the case for synthetic protide antigens, a short chain of amino acids can be used which will accommodate synthesis along two linear sequences. The short chain of amino acids of choice for such a synthesis, especially when the protide to be synthesized includes one or more lysine residues, takes the following general formula:

u-lys-v where u is either (1) the amino acid residue adjacent the N-terminus of lysine in the sequence of the protide to be synthesized, or (2) if it is not desired to synthesize a protide which includes the lysine residue, u is alanine, glycine, or other readily available, preferably charge neutral, amino acid. v is glycine, alanine, or other electrically neutral amino acid which is readily commercially available.

In the event it is desired to synthesize multiple epitopes or multiple chain synthetic protides using the short chain of amino acids, synthesis is accomplished through the ε-N of lysine as follows:

where B is the first synthetic protide to be synthesized, T is the second synthetic protide to be synthesized, and P is the remainder of the polymerized resin. For example, T and B could represent T-cell and B-cell epitopes, respectively, for inducing an immune response in an animal. Those skilled in the art who have the benefit of this disclosure will recognize that lysine is but one of several amino acids having an amino group in the side chain such that synthesis of the protide T can be accomplished on the amino acid sidechain. Other such amino acids include ornitbine, asparagine, glutamine, arginine, histidine, 5-hydroxylysine, desmosine, isodesmosine, and citrulline. The amino acids lysine, ornithine, and 5-hydroxylysine are, however, preferred because of their lack of electrical charge, absence of steric hindrance as a result of their relatively small side chains, and lack of any stabilizing double bonds which increase the difficulty of protecting and/or deprotecting the side chain amino group.

It will also be understood by those skilled in the art that the lysine, or other residue having an amino group within the side chain, could be coupled directly to the resin or OBA linker without the u and v amino acid residues. Either way, the resin is effectively double loaded such that it is possible to synthesize two protides from the same point of anchorage to the resin. The resin can even be used to synthesize two of the same protides simultaneously by, for instance, synthesizing the u-lys-v tripeptide with the Boc protecting group on the ε amino group of the lysine residue. The α amino group of the u amino acid is then protected with the fluorenylmethyloxycarbonyl (Fmoc) protecting group, the ε amino group of the Boc-protected lysine residue is deprotected, and an amino acid is substituted onto that ε amino group. The Fmoc protecting group is then removed from the α amino acid, both unprotected amino acids are contacted with the appropriately protected first amino acid in the protide to be synthesized, and synthesis then proceeds, as is known to those skilled in the art by repetitive deblocking, selective activation, and addition of amino acids in the desired sequence.

In the event it is desired to synthesize different protides at the same anchorage site, it may be necessary to use both Fmoc and Boc protecting groups. Further, additional protecting groups, stable to both Fmoc-based and Boc-based synthetic schemes, must be utilized. For instance, if it is desired to add lysine to the chain on which Fmoc-based schemes are being used, Fmoc and cbz (on the ε amino group) protecting groups are used, the cbz group being stable to both Fmoc and Boc chemistry. Selection of appropriate protecting groups in this fashion is generally within the skill of those skilled in the art.

The Boc-glycyl-4-(oxymethyl) benzoic acid which, when utilized, is the presently preferred linker was prepared by a modification of the method described by Mitchell, et al. (43 J. Org. Chem. 2845 (1978), which is incorporated herein in its totality by this specific reference thereto. An important modification of the Mitchell, et al., method is the elimination of the use of dimethylformamide as a solvent. That solvent is difficult to evaporate, consequently, even though evaporation can be hastened by raising the temperature, the method is still time-consuming. The 4-(bromomethyl)benzoic acid phenyl ester linker [3] was converted to the boc-glycyl derivative by reaction with the tetramethylammonium (TMA) salt of Boc-glycine:

The phenacyl ester [4] is reductively cleaved with zinc in 85% acetic acid to give the Boc-glycyl-(4-oxymethyl)benzoic acid [5] in overall yield of 85%.

The activator used to couple the linker to the polyamide resin prepared as described above is diisopropyl carbodiimide and 4-dimethylaminopyridine, but it will be understood by those skilled in the art that other activators such as dicyclohexylcarbodiimide (DCC) and 4-methylpyrrolidinopyridine are equally suitable for such a purpose. For instance, the compound [5] was anchored to the aminomethyl polydimethylacrylamide resin [2] using DCC activation with p-dimethylaminopyridine (DMAP) as catalyst.

After synthesis of the protide on the polyamide resin, the polyamide resin-protide conjugate is used for a number of purposes, including in vitro assays, inducing an immunogenic response in experimental animals, or mapping antigenic determinants. For instance, an in vitro assay is conducted by crushing the beaded polyamide resin-protide conjugate with a mortar and a pestle and absorbing the crushed conjugate onto a solid phase such as a microtiter test plate with neutral pH buffer. Serum or other body fluid suspected of containing an antibody capable of specifically binding the protein or peptide on the resin is then incubated with the absorbed conjugate, unbound antibodies are removed by washing, and the bound antibodies are detected by enzyme linked immunosorbent assay, biotin-avidin amplified assay or other detection methods such as are known in the art.

The polyamide resin-protide conjugate can also be used to map antigenic determinants by simply removing a portion of the polyamide resin-protide conjugate at intervals during the synthesis of the protide, deprotecting the protide, and testing each removed portion in serial fashion to determine that point in the synthesis at which the protide binds antibody. This method is made possible by the elimination of the separation and purification steps required in other synthetic methods. The conjugate can also be tested for its ability to bind antibody by crushing and absorbing to a solid support such as a microtiter test plate and assayed as described above.

Separation of the protide from the resin and purification of the protide is not required for such an assay.

The polyamide resin-protide conjugate is also useful as an immunogen. The conjugate is used directly for immunization with or without an adjuvant. For instance, an immune response specific for hepatitis B, as measured by radioimmunoassay, was induced by immunization of rabbits using a conjugate comprised of a synthetic peptide with the amino acid sequence of the hepatitis B surface antigen (HBsAG) peptide 119-159 emulsified in Freund's complete adjuvant. Similar results, as measured by radioimmunoprecipitation, were obtained with a conjugate comprising each of four peptides corresponding to portions of the protein coat of the AIDS virus HTLV-III and the improved polyamide resin of the present invention, with a conjugate comprising the resin and a peptide homologous to a rat fatty acid binding protein, a resin-peptide conjugate which included a peptide having a sequence homologous to the predicted sequence of a portion of the Abelson murine leukemia virus (ABL), and with two resin-peptide conjugates in which the peptide was homologous to a portion of the sequence of the protein portion of apolipoproteins B and C.

The present invention can be better understood by reference to the following examples, which are presented for purposes of exemplification and not limitation.

EXAMPLE I

Preparation of Allylamine Functional Monomer

Five grams of (26.8 mmol) 2-methylsulfonyl ethyloxycarbonyl chloride (MSC chloride) (K+K Labs, ICN) were dissolved in 15 ml acetonitrile and added dropwise over a 20 minute period to a stirred solution of 2.1 ml (28 mmol) redistilled allylamine (Kodak) and 4.9 ml (28 mmol) redistilled diisopropylethylamine (DIEA) in 20 ml acetonitrile. (DIEA (Aldrich) was refluxed over ninhydrin and redistilled.) The solution was stirred an additional two hours and the solvent evaporated. The residue was taken up in 250 ml ethyl acetate and allowed to stand for one-two hours. The bulk of the DIEA hydrochloride salt precipitated as needles. After filtration and evaporation, the crude material was dissolved in a minimal amount of chloroform and loaded onto a silica gel G-60 column (60 g) packed in the same solvent. Elution with chloroform yielded pure MSC-allylamine. ($R_F$ on TLC=0.64 (Solvent=CHCl$_3$: CH$_3$OH, 9:1).)

The remaining DIEA salts absorbed to the column under these conditions. Occasionally, material migrating near the solvent front on TLC contaminated the MSC-allylamine column fractions. That material was removed by crystallizing the MSC allylamine from methylene chloride-hexane at −20° C. Yield was 4.8 g (86% from MSC chloride).

EXAMPLE II

Preparation of Cross-Linker

The cross-linker N,N'-bisacrylyl-1,3-diaminopropane was prepared according to the method set out in Helpern and Sparrow, supra. Briefly, diaminopropane (Aldrich) was dissolved in acetonitrile and added dropwise to an acrylyl chloride-acetonitrile solution at 4° C., allowed to warm to room temperature and stirred. The diaminopropane dihydrochloride was removed by filtration, washed with warm acetonitrile, and the combined filtrates were concentrated in vacuo. N,N'-bisacrylyl-1,3-diaminopropane was crystallized at 4° C. overnight and the resulting plates filtered and dried in vacuo.

EXAMPLE III

Preparation of Polydimethylacrylamide Resin

In a glass, 2-liter cylindrical, fluted polymerization vessel fitted with a nitrogen inlet and mechanically driven glass stirrer were added 490 ml hexane and 290 ml carbon tetrachloride. The solution was purged for 15 minutes with nitrogen to remove oxygen. To this solution was added an aqueous solution containing N,N'-bisacrylyl-1,3-diaminopropane (2.9 grams, 15.9 mmol) prepared as described in Example II mixed with 18.2 ml (175 mmol) of N,N-dimethylacrylamide (PolySciences). Ten g (48 mmol) MSC allylamine prepared as described in Example I and 120 ml water were added, and the solution was filtered and degassed before addition to the organic phase. The density of the resulting mixture was adjusted to obtain a uniform suspension with stirring at 400–450 RPM. Ammonium persulfate (BioRad) (0.5 g in 5 ml $H_2O$) and 1 ml of either sorbitan sesquioleate or sorbitan monolaurate (Sigma) were added. A solution of 3 ml N,N,N',N'-tetramethylethylenediamine (TEMED) (BioRad) in 2 ml $H_2O$, pH 6.5–7.5 (conc. HCl) was then added to the suspension. The suspended emulsion was stirred for two hours under nitrogen atmosphere. The resultant beaded material was then filtered and washed sequentially with water (one liter) methanol (one liter), a mixture of dioxane:methanol:2N NaOH (14:5:1, two liters, to remove MSC group), water (two liters), 1N HCl (two liters), water (two liters), and then methanol (two liters). The resin was defined by suspension in methanol and decanting (3×). After swelling in methylene chloride (Baker HPLC grade), the resin was shrunk in hexane and dried in vacuo. Large amorphous material was removed by sifting the resin through an 80 mesh (180 micron) sieve.

The degree of functionalization was checked by coupling Boc-alanine to 100 mg of the resin using diisopropylcarbodiimide as activator and 4-dimethylaminopyridine (recrystallized from ethyl acetate) as catalyst. Amino acid analysis showed a substitution of 0.15 to 0.35 mmol/g resin, depending on the lot, and resins were prepared with as little as about 0.1 and as much as about 0.5 mmol/g resin depending upon the amount of allylamine added. The loaded resin gave no detectable staining with picryl-sulfonic acid, indicating the absence of unreacted free amine. When swollen in methylene chloride, the beads occupied about 2.5 times their dry bed volume. When swollen in dimethylformamide or an aqueous solution, the beads occupied approximately four and six times their dry bed volume, respectively.

EXAMPLE IV

Preparation of Aminohexyl Resin

An improved resin, which represents the presently preferred embodiment of the invention, was prepared as follows. A solution of 600 ml of carbon tetrachloride and 1070 ml of hexane was placed in a flask and stirred under nitrogen at about 600 rpm. A solution of 73 g of dimethylacrylamide (Poly Sciences), 11.2 g N,N-bisacryloyl-1,2-diaminopropane, and 18.16 g of N-acryloyl-1,6-diaminohexane hydrochloride in 500 ml of cold water was added to the organic solution and the density adjusted by adding hexane or carbon tetrachloride until the aqueous solution stayed suspended when the stirrer was stopped. A solution of 2 g of ammonium persulfate in 2 ml of water was then added, followed by about 1 ml of sorbitan laurate and a solution of 6 ml of TEMED in 6 ml of water, adjusted to pH 6.0 with 12N HCl. Polymerization was allowed to proceed for about 3 hours, after which the stirrer was stopped, hexane was added, the resin allowed to settle, and the organics removed by aspiration.

The resin was transferred to a two liter filter funnel, washed in methanol, water, and methanol, resuspended in methanol, and allowed to settle, and fine material was removed from the methanol by aspiration. After washing with 3×2 L dimethyl formamide and methylene chloride, stirring and washing with ethylacetate and hexane, the resin was dried in a vacuum dessicator and passed through an ASTM 80 mesh screen to obtain about 93 grams of resin. After neutralizing with 100 ml of 1N sodium hydroxide per gram of resin, washing with water, methanol, and methylene chloride, the loading was determined by amino acid analysis to be 0.7 mEq/g after coupling Boc-alanine to the resin.

EXAMPLE V

Preparation of Linker

The linker Boc-glycyl-4-(oxymethyl) benzoic acid was prepared by modification of the method of Mitchell, et al., supra. Briefly, the 4-(bromomethyl) benzoic acid phenylacylester was prepared by dissolving 10.3 ml redistilled diisopropylethylamine and 12.05 g (60.6 mmol) bromoacetophenone in 450 ml ethyl acetate. 4-(bromomethyl) benzoic acid (13.89 g, 60.6 mmol) was added in seven equal portions over a three hour period to the stirred solution at 40°–50° C. Stirring was continued for two more hours at room temperature. Precipitated $Et_3N$ HBr was removed by filtration and the ethyl acetate solution was washed four times with 50 ml each of an aqueous solution of 10% citric acid, saturated sodium chloride, saturated sodium bicarbonate, and saturated sodium chloride. The organic phase was dried over anhydrous magnesium sulfate and freed of solvent by rotary evaporation under reduced pressure. The residue was crystallized from $CH_2Cl_2$-petroleum ether (1:3 v/v) to give the 4-(bromomethyl) benzoic acid phenacylester.

The 4-(bromomethyl) benzoic acid phenacylester was converted to Boc-glycyl-4-(oxymethyl) benzoic acid by dissolving Boc-L-glycine (25 mmol, 4.38 g) in 15 ml methanol and titrating to neutrality with tetramethylammonium hydroxide (25% in methanol). Solvent was removed azeotropically with chloroform in vacuo, and the salt dissolved in 150 ml acetonitrile. To the stirred solution was added 5.8 g (17.5 mmol) of the 4-(bromomethyl) benzoic acid phenacyl ester prepared as described. After overnight mixing, the precipitated tetramethylammonium bromide was filtered and the solvent evaporated. The residue was dissolved in 400 ml ethyl acetate and the solution filtered. The organic phase was then washed successively with 10% aqueous citric acid (3×75 ml), 0.5M sodium bicarbonate: 0.5M potassium carbonate (2:1), pH 9.5 (8×75 ml), then water (3×75 ml). The solution was dried ($MgSO_4$) and the solvent removed in vacuo. The residue was dissolved in 200 ml of 85% acetic acid to which 23 g acid washed zinc dust was added. The mixture was stirred until the phenacyl ester was no longer visible by TLC (4-5 hours). The zinc was filtered and washed with 50 ml acetic acid, and the combined solutions were lyophilized. The residue was suspended in 100 ml water:300 ml ethyl acetate, and the pH adjusted to 1.5 (conc. HCl). The aqueous layer was extracted with a second portion of ethyl acetate (200 ml), and the combined extracts were washed with water (100 ml). After drying (MgSO4) and evaporating, the Boc-glycyl-4(oxymethyl) benzoic acid was purified by recrystallization from methylene chloride:hexane at −10°. Yield was 4.5 g (14.5 mmol, 83% from the phenacyl ester).

EXAMPLE VI

Coupling of Linker to Polyamide Resin

Boc-glycyl-4-(oxymethyl) benzoic acid prepared as described in Example V was coupled to the aminomethyl polyamide resin (1.2 g) prepared as described in Example III, as well as the aminohexyl resin prepared as described in Example IV, on a Biosearch Sam II automated peptide synthesizer using diisopropylcarbodiimide and dimethylaminopyridine as activator in a 1:1 methylene chloride:dimethylformamide solution. Both methylene chloride (Baker HPLC grade) and dimethylformamide (Baker Photrex grade) were used without further purification. Following treatment with hydrogen fluoride, 50 mg of the glycyl resin prepared as described in Example III was found to contain 0.13 mmol/g of linker by amino acid analysis. Amino acid analysis was performed using a Beckman Model 119 amino acid analyzer following either a two hour hydrolysis (12N HCl:propionic acid, 1:1, 135° C.) or 24 hour hydrolysis (6N HCl, 110° C.) of resin bound peptides.

EXAMPLE VII

Synthesis of Hepatitis B Antigen Peptide

The hepatitis B surface antigen (HBsAg) peptide 119-159 was assembled on the aminomethyl, crosslinked polydimethylacrylamide resin prepared as described in Example III, having the Boc-glycyl-4-(oxymethyl) benzoic acid linker prepared as described in Example V attached thereto using the method described in Example VI, with all residues being double coupled using a Biosearch Sam II automated peptide synthesizer. The sequence of that HBsAg peptide is as follows, and is relative to the AYW subtype:

The peptide included the following substitutions to control the specific formation of disulfide loops: serine for cysteines 121, 138, and 149. The cysteines 139 and 147 sulfhydryls were blocked by the 4-methoxybenzyl group, while the sulfhydryls of the cysteines at 124 and 137 were protected as the S-acetamidomethyl derivatives. α-N-tBoc protected amino acids were purchased from Bachem. Additional side chain protecting groups were as follows: formyl group for the indole nitrogen of tryptophan; benzylethers for threonine and serine hydroxyls; acetamidomethyl or 4-methoxybenzyl for cysteine sulfhydryls as described above; benzyl esters for β-carboxyl of aspartic acid and the γ-carboxyl of glutamic acid; 2-chlorobenzyloxycarbonyl for ε-amino group of lysine; 2,6-dichlorobenzyl ether for the phenolic hydroxyl of tyrosine; and the p-tosyl group for the guanidine of arginine. For the synthesis, methylene chloride (Baker HPLC grade) and DMF (Baker Photrex grade) were used without further purification. Diisopropylethylamine (DIEA) (Aldrich) was refluxed over ninhydrin and redistilled. Trifluoroacetic acid (Halocarbon) was redistilled, with the middle cut used in deblocking steps. All other chemicals were reagent grade or better and used without further purification.

Side chain protecting groups were removed from the completed peptidyl-resin by treatment with anhydrous HF (20 ml/g resin) at 0° for thirty minutes, containing 10% anisole and 2% ethanedithiol. Following evaporation of HF, the peptidyl-resin was washed successively with ether, 1% acetic acid, methanol, 5% DIEA in methylene chloride, methanol, then water. The peptidyl-resin was dried in vacuo. The formyl group was removed from the tryptophan by treatment with 1M ethanolamine at 0°. A disulfide bridge was formed between cysteines 139 and 147 by potassium ferricyanide treatment. A second disulfide bridge between cysteines 124 and 137 resulted during simultaneous removal of the acetimidomethyl moieties with a solution of iodine in acetic acid.

EXAMPLE VIII

In Vitro Assay for Presence of HBsAg Antibody

Human serum is assayed for the presence of antibody specific for the HBsAg peptide 119-159 by the following in vitro assay. A quantity of the HBsAg peptide 119-159-polyamide resin conjugate prepared as described in Example VI is crushed with a mortar and pestle. A microscope may be used to verify that the polyamide resin-peptide conjugate has been crushed. Approximately 100 μl of a solution containing between about 200 nanograms and about 10 micrograms of the crushed polyamide resin-peptide conjugate in a neutral pH buffer such as phosphate buffered saline (PBS) is absorbed to a solid phase such as Dynatech Immunolon II Microtiter test plates. Nonspecific binding sites are blocked with 10% normal goat serum (NGtS) and the plate is washed with Tween 20 PBS (T-PBS) to remove unbound antibodies.

Human sera suspected of containing antibodies specific for HBsAg peptide 119-159 and rabbit antisera produced by immunizing rabbits with the polyamide resin-HBsAg peptide 119-159 conjugate diluted in 10% NGtS is then added to the polyamide resin-peptide-coated plate and incubated for one hour at 37° C., followed by washing with T-PBS. Biotin goat anti-human IgG or biotin goat anti-rabbit IgG (Vector Laboratories, Burlingame, CA) is then incubated with the bound human and rabbit sera, respectively, for one hour at 37° C. The wells are washed and avidin conjugated to horseradish peroxidase (Av-HRP) is added for 20 minutes at room temperature. The wells are then washed with T-PBS to remove any unbound Av-HRP, and peroxidase activity is determined using a 1 mM solution of 1,2'-azino-di(3-ethyl-benzthiazoline sulfonic acid) (Sigma Chemical Co.) and 0.03% $H_2O_2$ as substrate. The reaction is stopped with 5% (w/v) sodium dodecyl sulfate in water prior to quantitating spectrophotometrically at 410 nm using a Dynatech plate reader. Optimal dilutions of each reagent are selected by titration. All reagents for determining specific binding except the substrate are diluted in 10% NGtS.

EXAMPLE IX

In Vitro Assay for Presence of HBsAg Antibody

Human serum was assayed for the presence of antibody to hepatitis B surface antigen by the following in vitro assay. A 10% solution of the polyamide resin-HBsAg peptide 119-159 conjugate was prepared in a buffered bovine serum albumin (BSA) solution containing a final concentration of 40% tetrahydrofuran. An equal volume of antibody specific for the HBsAg peptide 119-159 containing between 100,000 and 1,000,000 counts per minute $I^{125}$ was added and incubated with gentle rocking. The resulting suspension was centrifuged and the pellet washed with 1% BSA-Tween 20 PBS, then centrifuged again. The radioactivity of the pellet was then counted in a Gamma counter. The results clearly indicate the recognition of the polyamide resin-HbsAg peptide 119-159 conjugate by native HBsAg antibody:

| | Glycyl resin (Control) | resin-HbsAg peptide 119-159 conjugate |
|---|---|---|
| IgG Human anti-HB#1 | 1240 cpm* | 22,840 |
| IgG Human anti-HB#2 | 1921 | 28,732 |
| Normal human IgG | 1432 | 1949 |

*all measurements in counts per minute

EXAMPLE X

Use of Polyamide Resin-Protide Conjugate to Induce an Immunogenic Response in Mammals The polyamide resin-peptide conjugate prepared as described in Example VII was used to induce an immunogenic response in rabbits as follows. New Zealand white female rabbits were immunized with three monthly intramuscular injections of either 200 μg HBsAg peptide 119-159 (as the peptide-resin conjugate) or only glycyl-resin emulsified in Freund's complete adjuvant (range of immunogen, 50 μg to 1 mg for rabbits). Serum was collected after bi-weekly bleeding and checked for anti-HBsAg activity using a commercially available radioimmunoassay (RIA) kit (AUSAB, Abbott Laboratories). The recognition of the native HBsAg surface antigen by the anti-peptide 119-159 antibody response induced in the rabbits is demonstrated by the following data developed by that RIA.

| RABBIT | IMMUNOGEN | IMMUNIZATION | ANTIBODY TITER[a] (RIA UNITS PER MILLILITER) |
|---|---|---|---|
| No. 1 | Glycine-Resin | Preimmune[a] | ≦8[b] |
| | | Primary | ≦8 |
| | | Secondary | ≦8 |
| | | Tertiary | ≦8 |
| No. 2 | HBsAg Peptide-Resin | Preimmune | ≦8 |
| | | Primary | ≦8 |
| | | Secondary | 183 |
| | | Tertiary | 920 |
| No. 3 | HBsAg Peptide-Resin | Preimmune | ≦8 |
| | | Primary | ≦8 |
| | | Secondary | 72 |
| | | Tertiary | 262 |

[a]Sera obtained prior to immunization.
[b]Antibody titer to HBsAg is below the sensitivity of the RIA kit and is considered not to contain specific antibodies.

As can be seen by these data, the polyamide resin-HBsAg peptide 119-159 conjugate containing a single disulfide bridge between cysteines 139 and 147, when used to immunize rabbits, yielded anti-peptide antisera which cross reacted with HBsAg.

EXAMPLE XI

SYNTHESIS OF HTLV-III ANTIGEN PEPTIDE

A portion of the HTLV-III envelope glycoprotein gp120, specifically, the amino acid sequence between residue numbers 503-532, was assembled on the cross-linked polydimethylacrylamide resin prepared as described in Example III, having the Boc-glycyl-4-(oxymethyl) benzoic acid linker prepared as described in Example V attached thereto using the method as described in Example VI, in the same method as described for the synthesis of the HBsAG peptide 119-159 in Example VII, the only difference being the order in which the protected amino acids were added. The sequence of the HTLV-III peptide gp120 503-532 is as follows:

$H_2N$—VAL—ALA—PRO—THR—LYS—ALA—LYS—
503

ARG—ARG—VAL—VAL—GLN—ARG—GLU—

LYS—ARG—ALA—VAL—GLY—ILE—GLY—ALA—

LEU—PHE—LEU—GLY—PHE—LEU—GLY—

Using the same method, three additional peptide-resin conjugates have been prepared which include the following amino acid sequences which are homologous to portions of the envelope glycoprotein of HTLV-III, each identified by their respective residue numbers:

| Sequence | Homologous To |
|---|---|
| 304-327 | gp120 |
| 341-370 | gp120 |
| 733-756 | gp41 |

EXAMPLE XII

ABILITY OF HTLV-III PEPTIDE-RESIN CONJUGATES TO BIND TO HUMAN ANTI-HIV ANTIBODIES

HTLV-III is one of several strains of retrovirus which have been implicated as the causative agent of human Acquired Immunodeficiency Syndrome, or AIDS, all of which are referred to as Human Immunodeficiency Virus, or HIV. To test the immunogenicity of the peptide-resin conjugate of the present invention, the four conjugates having peptides homologous to portions of the envelope glycoprotein of HTLV-III prepared as described in Example XI were tested against serum samples taken from 110 HIV-infected individuals for their ability to bind anti-HIV antibodies. That assay was conducted as follows.

Samples of each conjugate (2 µg) were absorbed to Dynatech Immunolon microtiter test plates in borate buffered saline (BBS), pH 8.2, overnight at 4° C. Non-specific sites were blocked with 200 µl 10% normal goat serum (NGtS) in Tween 20 phosphate buffered saline (T-PBS) for 20 minutes at room temperature and then washed three times with T-PBS. Biotin goat anti-human IgG (Vector Laboratories, Burlingame, CA) was then incubated with the bound human sera for one hour at 37° C. Wells were washed three times and avidin conjugated to horseradish peroxidase (Av-HRP) was added for 20 minutes at room temperature. The wells were again washed three times with T-PBS and peroxidase activity determined using a 1 mM solution of 1,2′-azino-di(ethylbenzthiazoline-sulfonic acid) (Sigma Chemical Co.) with 0.03% $H_2O_2$ as the substrate. The reaction was stopped with 5% (w/v) sodium dodecyl sulfate in water and optical density read at 410 nm using a Dynatech plate reader. Optimal dilutions were selected by titration. The results were as follows, where a positive result was defined as an optical density three standard deviations above the mean optical density obtained with 20 seronegative samples.

| Peptide Sequence | No. Individuals | No. Positive |
|---|---|---|
| 304–327 | 26 | 24 |
| 341–370 | 33 | 30 |
| 503–532 | 44 | 40 |
| 733–756 | 24 | 22 |

EXAMPLE XIII

Figure 1:
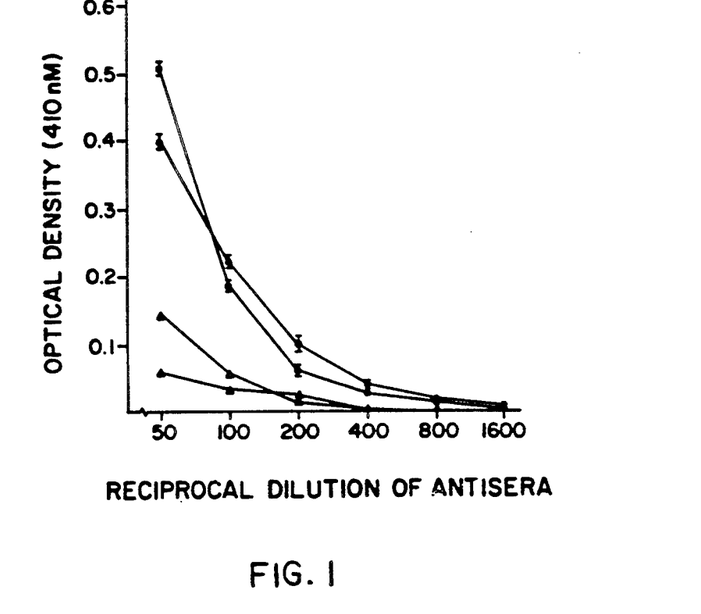
FIG. 1 is a graph of optical density at 410 nm as a function of the reciprocal dilution of rabbit antisera to the polyamide resin-HTLV-III peptide 503-532 conjugate obtained by enzyme linked immunosorbent assay (ELISA). The circles represent data from rabbits immunized with that conjugate, the triangles represent data from those same rabbits before immunization.

Use of Polyamide Resin-HTLV-III Synthetic Peptide Conjugate to Induce an Immunogenic Response Rabbits immunized with the polyamide resin-HTLV-III peptide 503–532 conjugate produced a specific anti-peptide response as determined by an enzyme linked immunosorbent assay conducted according to the method of Examples VIII (with the use of antisera produced by immunizing the rabbits with the polyamide resin-HTLV-III peptide 503–532 conjugate rather than the conjugate which included the HBsAg peptide 119–159 as used in that Example) and XII. The results of that immunoassay are presented graphically in FIG. 1. The data represented by the circles is data from rabbits immunized with that conjugate, the data represented by triangles is from those same rabbits before immunization (the solid circles and triangles are both from one rabbit; the open circles and triangles are both from a second rabbit). A conjugate comprised of the polyamide resin and a third peptide failed to demonstrate significant binding. One of the rabbits produced an anti-HTLV-III response specific for the gp120 envelope protein of HTLV-III based on a radioimmunoprecipitation assay conducted according to the method of Allan, J. S., et al. 228 Science 1091 (1985) and Barin, F., et al., 228 Science 1094 (1985), both of which are incorporated herein in their entirety by this specific reference thereto.

The ability of the rabbit antisera generated to peptide 503–532 to neutralize HTLV-III infectivity was assessed on the basis of a reduction of reverse transcriptase activity using a tenfold dilution of the HTLV-III stock with a constant amount of antisera. Barre-Sinoussi, F., et al., 220 Science 868 (1983). A single rabbit anti-peptide 503–532 antiserum efficiently reduced HTLV-III replication at day 10 compared to pooled human sera from AIDS patients at tenfold dilutions of virus. A second rabbit antiserum to that peptide failed to reduce HTLV-III replication and so was used as a control throughout the RT assay. No anti-HTLV-III activity was detected in this particular antiserum based on radioimmunoprecipitation even though the rabbit received a similar immunogen and produced a detectable anti-peptide response.

The antiserum that neutralized HTLV-III detected both gp120 and gp160 envelope glycoproteins. This rabbit antiserum was found to be less efficient in neutralizing HTLV-III compared to human AIDS serum on day 12 and 15 following HTLV-III infection.

EXAMPLE XIV

Production of Antibodies Using Peptide-Resin Conjugates

To further test the immunogenicity of the peptide-resin conjugates of the present invention, four additional peptide-resin conjugates were prepared, injected into rabbits, and the sera checked for the presence of antibody against the respective native proteins. Those peptide-resin conjugates were prepared in the same manner as set out in Example VII, and included the following peptides:

(a) a peptide having a sequence homologous to a portion of the amino acid sequence of the rat fatty acid binding protein residue numbers 22–34 (FABP) (see Chan, L., et al., 260 J. Biol. Chem. 2629 (1985));

(b) a peptide having a sequence homologous to a portion of the predicted amino acid sequence of the murine Abelson leukemia virus (abl 389–403) (see E. Reddy, et al., 80 Proc. Nat'l. Acad. Sci. USA 3617 (1983));

(c) a peptide having a sequence homologous to a portion of the amino acid sequence of the apolipoprotein C-II, residue numbers 56–69 (Apo C-II) (see Hospattanker, A. V., et al., 259 J. Biol. Chem. 318 (1984)); and (d) a peptide having a sequence homologous to a portion of the amino acid sequence of the apolipoprotein B, residue numbers 3357–3369 (Apo B) (see Yang, C.-Y., et al., 323 Nature 738 (1986)).

Peptides were coupled directly to the aminohexyl resin prepared as described in Example IV containing 0.70 mM of glycine per gram of resin for synthesis. Once synthesis was completed, the resins were dried and 0.5 g of each resin sample was treated with 10 ml anhydrous HF containing 10% anisole and 1% ethanedithiol for 30 minutes at 0° C. The HF was evaporated under vacuum at 0° C. and the resin was transferred to a glass filter funnel with ether, washed with 3×50 ml each of ether, methanol, water, 1% acetic acid, water, 0.1M Tris, water, 1% acetic acid and water to neutrality, and then dried in a vacuum dessicator. The amino acid composition of each sample was determined by hydrolysis with 12N HCl: propionic acid (1:1) at 135° C. for two hours and analyzed on a Beckman 6300 amino acid analyzer. Amino acid sequences of each peptide were determined with either an Applied Biosystems Model 470A or 477A protein sequencer.

Samples of each peptidyl-resin (1 mg) were swollen in 100 μl of sterile normal saline and crushed with an homogenizer. After mixing with an equal volume of incomplete Freund's adjuvant, the mixtures were injected into New Zealand white rabbits at multiple sites. After two weeks, serum was obtained from an ear vein and checked with a ELISA for antibody against the native protein. Rabbits were then boosted with mixtures prepared in this same manner and the process repeated over two months. Antibody titers after the two months, determined against native proteins (not the respective peptide) were as follows:

| Peptide | Antibody Titer |
| --- | --- |
| FABP | 900 |
| ABL-389 | 64 |
| Apo C-II | 250 |
| Apo B | 50 |

The experiment was repeated after synthesizing a T-cell epitope from Staph. aureus nuclease having the following amino acid sequence:

lys-met-val-glu-asp-ala-lys

The T-cell epitope was added synthetically to the amino terminal of the remaining peptidyl-resin conjugate for each of the peptides, viz., FABP, ABL-389, Apo C-II, and Apo B. The remaining steps were repeated exactly as above. The following antibody titers were found:

| Peptide | Antibody Titer |
| --- | --- |
| FABP | 2500 |
| ABL-389 | 2550 |
| Apo C-II | 1250 |
| Apo B | 250 |

In a second set of tests, the ABL-resin and FABP resin conjugates were ground in a tight-fit homogenizer with 20 strokes and 500 μg of the ground conjugate was suspended in 1.5 ml of phosphate buffered saline (PBS) and emulsified with another 1.5 ml of Freund's complete adjuvant. The rabbits were injected subcutaneously at multiple sites, and two booster injections of each PBS-conjugate suspension in Freund's incomplete adjuvant were given at two week intervals. Two weeks after the second booster, the rabbits were bled and anti-peptide titer assayed in an ELISA against the respective peptide of the resin-peptide conjugate.

The ELISA was conducted by plating 50 ng of each peptide in 0.1M NaHCO$_3$, pH 9, in the wells of a 96-well test plate and drying overnight at 37° C. Nonspecific sites were blocked with a TN solution of 50 mM Tris-HCl, pH 7.6 and 50 mM NaCl with 5% nonfat dry milk for one hour at 37° C. Sera (50 μl) was added in serial dilution to each well and incubated at 37° C. for one hour. Plates were washed 6 times with TN solution with 0.05% Tween 10 (Sigma). Fifty μl of peroxidase conjugated goat anti-rabbit IgG (1:4000) (Boehringer Mannheim Biochemicals) in TN buffer with 5% nonfat dry milk were added to each well, and after incubating for one hour, plates were washed six times with TN solution. Fifty μl of o-phenyline-diamine (OPD) (Sigma) was added to each well as substrate and incubated for 20 minutes at room temperature.

Figure 2:
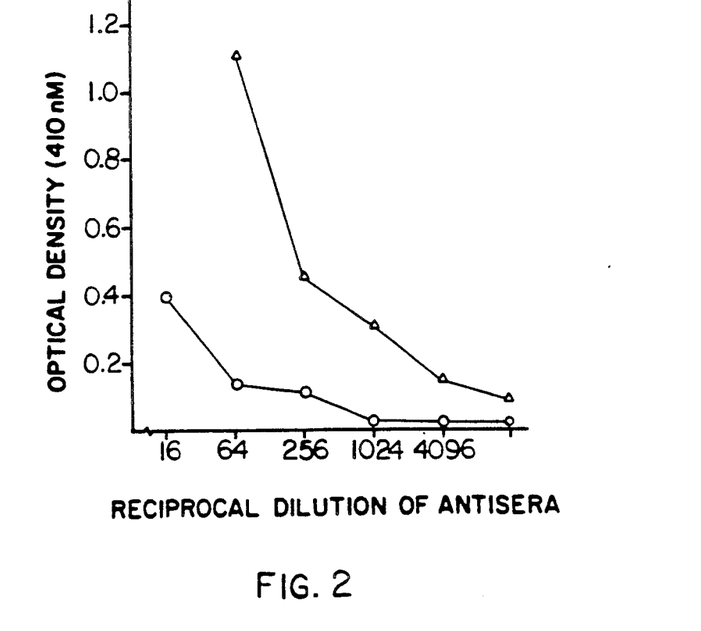
FIG. 2 is a graph of optical density at 492 nm as a function of the concentration of antisera obtained from rabbits injected with the polyamide resin-ABL peptide and polyamide resin-FABP peptide conjugates obtained by ELISA. The circles represent data from rabbits immunized with the resin-ABL conjugate, the triangles represent data from rabbits immunized with the FABP-resin conjugate.

Plates were read at 495 nm in an ELISA autoreader as a net value in which the OD reading of the pre-immune sera was substrated from the OD reading of the immune sera. Optical density is plotted as a function of serum concentration in FIG. 2. Each data point represents the average of three rabbits. The circles represent the data from rabbits immunized with the ABL-resin conjugate and the triangle represents data from rabbits immunized with the FABP-resin conjugate.

The foregoing examples are presented for purposes of exemplification of the method of the present invention. Variations in those methods will be known to those skilled in the art, and it is expected that all such variations will be made without departing from the spirit and scope of the present invention as claimed in the following claims.

What is claimed is:

1. A polyamide resin-bound protide, comprising
    a cross-linked aminoalkyl polydimethylacrylamide resin-bound protide.

2. The polyamide resin-bound protide of claim 1, wherein
    the resin-bound protide is selected from the group consisting of immunogenic peptides and proteins, antigenic fragments thereof and combinations thereof.

3. The polyamide resin-bound protide of claim 2, wherein
    the resin-bound protide comprises a peptide selected from the group consisting of aminoalkyl cross-linked polydimethylacrylamide resin-bound amino acids 304-327, 341-370 and 503-532 of the gp120 HTLV-III envelope glycoprotein and amino acids 733-756 of the gp41 HTLV-III glycorpotein, antigenic fragments thereof and combinations thereof, and amino acids 119-159 of the hepatitis B surface antigen, antigenic fragments thereof and combinations thereof.

4. The polyamide resin-bound protide of claim 3, wherein
    the cross-linked polydimethylacrylamide resin-bound protide comprises amino acids 304-327 of the gp120 HTLV-III envelope glycoprotein, antigenic fragments thereof or combinations thereof.

5. The polyamide resin-bound protide of claim 3, wherein
    the cross-linked polydimethylacrylamide resin-bound peptide comprises amino acids 341-370 of the gp120 HTLV-III envelope glycoprotein, antigenic fragments thereof or combinations thereof.

6. The polyamide resin-bound protide of claim 3, wherein
    the cross-linked polydimethylacrylamide resin-bound peptide comprises amino acids 503-532 of the gp120 HTLV-III envelope glycoprotein, antigenic fragments thereof or combinations thereof.

7. The polyamide resin-bound protide of claim 3, wherein the cross-linked polydimethylacrylamide resin-bound peptide comprises amino acids 733-756 of the gp41 HTLV-III glycoprotein, antigenic fragments thereof or combinations thereof.

8. The polyamide resin-bound protide of claim 3, wherein the cross-linked polydimethylacrylamide resin-bound peptide comprises amino acids 119-159 of the hepatitis B surface antigen, antigenic fragments thereof and combinations thereof.

9. The polyamide resin-bound protide of claim 1, comprising the cross-linked resin is selected from the group consisting of diaminoalkane cross-linked polydimethylacrylamide resins, and diaminoalkane cross-linked, oxyalkylbenzoic acid derivative-linked polydimethylacrylamide resins.

10. An immunogenic composition, comprising an immunogenic amount of the polyamide resin-bound protide of claim 2; and a pharmaceutically-acceptable carrier.

11. The immunogenic composition of claim 10, further comprising an adjuvant.

12. A method of synthesizing the polyamide resin-bound protide of claim 1, comprising obtaining a cross-linked poly-N-acrylaldiaminoalkane-dimethylacrylamide resin; and forming the protide on the resin.

13. The method of claim 12, wherein the polyamide resin is cross-linked with a diaminoalkane.

14. The method of claim 13, wherein the diaminoalkane cross-linking the resin comprises a N,N'-bisalkenoyl-diaminoalkane.

15. The method of claim 14, wherein the N,N'-bisalkenoyl-diaminoalkane cross-linking the resin is selected from the group consisting of N,N'-bisacrylyl-1,3-diaminopropane, N,N'-bisacrylyl-1,2-diaminoethane, N,N'-bisacrylyl-1,4-diaminobutane and N,N'-bisacrylyl-1,6-diaminohexane.

16. The method of claim 12, further comprising coupling a linker to the polyamide resin prior to the protide forming step.

17. The method of claim 15, wherein in the coupling step, the linker comprises an oxyalkyl benzoic acid derivative.

18. The method of claim 12, further comprising filtering, washing, and drying the resin prior to the protide forming step.

19. The method of claim 12, wherein the resin on which the protide is formed comprises beads.

20. The method of claim 12, wherein the cross-linked polyamide resin on which the protide is formed comprises poly-N-acrylyl-1,6-diaminohexane-dimethylacrylamide.

21. The method of claim 12, wherein the cross-linked polyamide resin on which the protide is formed comprises a bisalkenoyl-diaminoalkane cross-linked poly-N,N'-1,6-diaminohexane-dimethylacrylamide resin.

22. The method of claim 12, wherein the cross-linked polyamide resin on which the protide is formed comprises an oxyalkylbenzoic acid derivative-linked N,N'-1,6-diaminohexane-dimethylacrylamide cross-linked resin.

* * * * *